(12) United States Patent
Miyashita

(10) Patent No.: US 11,963,532 B2
(45) Date of Patent: Apr. 23, 2024

(54) USE OF MICROORGANISM TO IMPROVE PLANT PRODUCTIVITY OF SOIL

(71) Applicant: MOSIL CO., LTD., Chiba (JP)

(72) Inventor: Hiroki Miyashita, Tokyo (JP)

(73) Assignee: MOSIL CO., LTD. (JP)

( * ) Notice: Subject to any disclaimer, the term of this patent is extended or adjusted under 35 U.S.C. 154(b) by 0 days.

(21) Appl. No.: 17/761,490

(22) PCT Filed: Oct. 1, 2020

(86) PCT No.: PCT/JP2020/037476
§ 371 (c)(1),
(2) Date: Mar. 17, 2022

(87) PCT Pub. No.: WO2021/066115
PCT Pub. Date: Apr. 8, 2021

(65) Prior Publication Data
US 2022/0361505 A1 Nov. 17, 2022

(30) Foreign Application Priority Data

Oct. 2, 2019 (JP) .................................. 2019-182447

(51) Int. Cl.
*A01P 21/00* (2006.01)
*A01G 22/15* (2018.01)
*A01N 63/22* (2020.01)

(52) U.S. Cl.
CPC ............. *A01N 63/22* (2020.01); *A01G 22/15* (2018.02); *A01P 21/00* (2021.08)

(58) Field of Classification Search
CPC ......... A01G 22/15; A01G 24/22; A01P 21/00; C12N 1/205; C12R 2001/01
See application file for complete search history.

(56) References Cited

U.S. PATENT DOCUMENTS

| 2011/0011141 A1* | 1/2011 | Hepburn | ................... | C05F 3/00 71/8 |
| 2016/0143295 A1 | 5/2016 | Hirsch et al. | | |

FOREIGN PATENT DOCUMENTS

| CN | 101473853 A | 7/2009 |
| CN | 106433680 A | 2/2017 |
| JP | H9-227323 A | 9/1997 |
| JP | 2018-502869 A | 2/2018 |
| KR | 10-2017-0043768 A | 4/2017 |
| WO | 2016115468 A1 | 7/2016 |
| WO | 2016130586 A2 | 8/2016 |

OTHER PUBLICATIONS

35 TheSchumann, P., Stackebrandt, E. (2014). The Family Promicromonosporaceae . In: Rosenberg, E., DeLong, E.F., Lory, S., Stackebrandt, E., Thompson, F. (eds) The Prokaryotes. Springer, Berlin, Heidelberg. doi.org/10.1007/978-3-642-30138-4_173. pp. 701-724. (Year: 2014).*
Dmitrenok et al., Carbohydr Res. Sep. 8, 2017;449:134-142. doi: 10.1016/j.carres.2017.07.008. Epub Jul. 27, 2017. PMID: 28783569. (Year: 2017).*
Wang et al. "Soil productivity and structure of bacterial and fungal communities in unfertilized arable soil", PLoS One. 2018;13(9):e0204085. Published Sep. 24, 2018, 17 pages.
Fujita et al. "Source-sink manipulation of *Camelina sativa* L. related to grain yield under stressful environment of Hokkaido, Japan", Soil Science and Plant Nutrition, 60, 156-161 (2014), 7 pages.
Kumar et al. "Paclobutrazol treatment as a potential strategy for higher seed and oil yield in field-grown *Camelina sativa* L. Crantz", BMC Research Notes, 5,137 (2012), 14 pages.
Mohammed et al. "Nutrient Requirements of Camelina for Biodiesel Feedstock in Central Montana", Agronomy Journal, 109, 309-316 (2017).
Czarnik et al. "The effects of varied plant density and nitrogen fertilization on quantity and quality yield of *Camelina saliva* L.", Emirates Journal of Food and Agriculture, 29, 988-993 (2017).
Waraich et al., "*Camelina sativa*, a climate proof crop, has high nutritive value and multiple-uses: a review", Australian Journal of Crop Science, 7,1551-1559 (2013).
Pheomphun et al., "Contribution of Bacillus cereus ERBP in ozone detoxification by Zamioculcas zamiifolia plants: Effect of ascorbate peroxidase, catalase and total flavonoid contents for ozone detoxification", Ecotoxicology and Environmental Safety, Jan. 17, 2019, 2019, vol. 171, pp. 805-812.
Ahmad et al., "Combined application of compost and *Bacillus* sp. CIK-512 ameliorated the lead toxicity in radish by regulating the homeostasis of antioxidants and lead", Ecotoxicology and Environmental Safety, Nov. 28, 2017, 2018, vol. 148, pp. 805-812.
International Search Report mailed Dec. 8, 2020 for PCT/US2020/037476, 5 pages.
Muhammad et al., "Synergistic Use of Rhizobium, Compost and Nitrogen to Improve Growth and Yield of Mungbean (*Vigna radiata*)", Pakistan Journal of Agricultural Sciences, vol. 51, No. 1, Jun. 2014, pp. 393-398.
Ying et al., "Contrasting beneficial and pathogenic microbial communities across consecutive cropping fields of greenhouse strawberry", Applied Microbiology and Biotechnology, vol. 102, No. 13, Apr. 27, 2018, pp. 5717-5729.

* cited by examiner

*Primary Examiner* — Kade Ariani
(74) *Attorney, Agent, or Firm* — Fox Rothschild LLP

(57) ABSTRACT

Soil plant productivity is improved by manipulation of soil microflora. The soil microflora is manipulated by addition of a bacterium belonging to *Rhizobium* (Rhizobiales) to the soil.

1 Claim, 2 Drawing Sheets
Specification includes a Sequence Listing.

| | AVERAGE (g) | S.D. |
|---|---|---|
| TEST PLOT | 4.46 | 0.10 |
| CONTROL PLOT | 2.65 | 0.27 |

USE OF MICROORGANISM TO IMPROVE PLANT PRODUCTIVITY OF SOIL

CROSS-REFERENCE TO RELATED APPLICATIONS

This application is a U.S. national phase application under 35 U.S.C. § 371 of International Patent Application No. PCT/JP2020/037476 filed Oct. 1, 2020, which claims the benefit of priority to Japanese Patent Application No. 2019-182447 filed Oct. 2, 2019, the disclosures of which are hereby incorporated by reference herein in their entireties.

FIELD

The present invention relates to a composition, method and compost for improving soil plant productivity using microorganisms belonging to the genus Rhizobium (Rhizobiales), and to a composition, microorganism and compost for increasing antioxidant activity of plants.

BACKGROUND

Ammonia and lime nitrogen produced by industrial nitrogen fixation are nitrogenous chemical fertilizers or fertilizer starting materials that are currently in wide use for crop cultivation in the agriculture industry. However, because the energy required for some of the reaction substrates and reactions used in industrial nitrogen fixation is dependent on fossil fuels, their long-term sustainability is limited. Large-scale use of fossil carbon sources is one factor impairing the stability of the environment. Since techniques that promote the agricultural use of biological nitrogen fixation are therefore indispensable for long-term agricultural systems, a great deal of research has been conducted to date in regard to microorganisms that promote plant growth by supplying nitrogen to plants.

Soil microflora are known to affect soil plant productivity, and specifically it has been reported that the abundance ratio of bacteria belonging to Rhizobium (Rhizobiales) or iii1-15 positively correlates with soil plant productivity, while the abundance ratio of bacteria belonging to Acidobacterium (Acidobacteriales) or Solibacterium (Solibacterales) negatively correlates with soil plant productivity (NPL 1). As of the current time, however, no method for artificially manipulating soil microflora has yet been established, and it has therefore been difficult to improve soil plant productivity in this manner.

CITATION LIST

Non Patent Literature

[NPL 1] Wang et al., PLoS One, 13, e0204085(2018)
[NPL 2] Fujita et al., Soil Science and Plant Nutrition, 60, 156-161(2014)
[NPL 3] Kumar et al., BMC Research Notes, 5,137(2012)
[NPL 4] Mohammed et al., Agronomy Journal, 109, 309-316(2017)
[NPL 5] Czamik et al., Emirates Journal of Food and Agriculture, 29, 988-993(2017)
[NPL 6] Waraich et al., Australian Journal of Crop Science, 7, 1551-1559(2013)

SUMMARY

Technical Problem

The problem to be solved by the invention is to improve soil plant productivity by manipulation of soil microflora, and to thereby increase the antioxidant activity of plants to improve plant productivity and harvest quality.

Solution to Problem

As a result of avid research and experimentation with the goal of solving this problem, the present inventors have surprisingly found that it is possible to alter soil microflora and thereby significantly improve plant productivity, if bacteria belonging to the genus Rhizobium (Rhizobiales) is added to the soil. The present inventors further found, surprisingly, that bacteria belonging to the genera Bacillus (Bacillales), Promicromonospora and Olivibacter increase the antioxidant activity of plants. The invention has been completed upon these findings.

Specifically, the present invention provides the following.

[1] A composition for improving soil plant productivity, comprising a bacterium belonging to Rhizobium (Rhizobiales).

[2] A method for improving soil plant productivity, wherein a bacterium belonging to Rhizobium (Rhizobiales) is added to soil.

[3] The method according to [2], wherein the plant is a Brassicaceae plant.

[4] The method according to [3], wherein the Brassicaceae plant is camelina or komatsuna.

[5] The method according to any one of [2] to [4], wherein the improvement in soil plant productivity results in an increased number of sheaths per plant, an increased number of seeds per plant and/or increased plant body weight.

[6] A compost comprising a bacterium belonging to Rhizobium (Rhizobiales), and a bacterium belonging to Actinomyces (Actinomycetales), a bacterium belonging to Bacillus (Bacillales), a bacterium belonging to Gaiellales, a bacterium belonging to Myxococcus (Myxococcales), a bacterium belonging to iii1-15, a bacterium belonging to Solirubrobacterales, a bacterium belonging to Xanthomonas (Xanthomonadales), a bacterium belonging to Burkholderia (Burkholderiales) and a bacterium belonging to Gemmatales.

[7] The compost according to [6], wherein the abundance ratio of bacteria belonging to Rhizobium (Rhizobiales) in the compost is 9% or higher, and the abundance ratio of bacteria belonging to iii1-15 is 6% or lower.

[8] The compost according to [6] or [7], which is for cultivation of Brassicaceae plants.

[9] The compost according to [8], wherein the Brassicaceae plant is camelina or komatsuna.

[10] A composition for increasing the antioxidant activity of plants, comprising a bacterium belonging to Bacillus (Bacillales), Promicromonospora or Olivibacter.

[11] The composition according to [10], wherein the bacterium belonging to Bacillus (Bacillales), is Bacillus cereus, the bacterium belonging to Promicromonospora is Promicromonospora citrea, and the bacterium belonging to Olivibacter is Olivibacter sp.

[12] The composition according to [11], wherein the Bacillus cereus is the strain deposited at the NITE Patent Microorganisms Depositary as deposit number NITE BP-02974, the Promicromonospora citrea is the strain deposited at the NITE Patent Microorganisms Depositary as deposit number NITE BP-03025, and the Olivibacter sp. is the strain deposited at the NITE Patent Microorganisms Depositary as deposit number NITE BP-03026.

[13] The bacterial strain deposited at the NITE Patent Microorganisms Depositary as deposit number NITE BP-02974.

[14] The bacterial strain deposited at the NITE Patent Microorganisms Depositary as deposit number NITE BP-03025.

[15] The bacterial strain deposited at the NITE Patent Microorganisms Depositary as deposit number NITE BP-03026.

[16] A compost comprising a bacterial strain according to any one of [13] to [15].

Advantageous Effects of Invention

According to the invention, soil plant productivity is improved and the number of sheaths per plant, the number of seeds per plant and/or the weight of the plant body are increased, thereby making it possible to significantly improve plant yields and to increase the antioxidant activity of plants, and thus to significantly improve plant productivity in relation to oxidative stress and quality of harvests (such as functionality, disease resistance and storage life).

DESCRIPTION OF EMBODIMENTS

Figure 1:
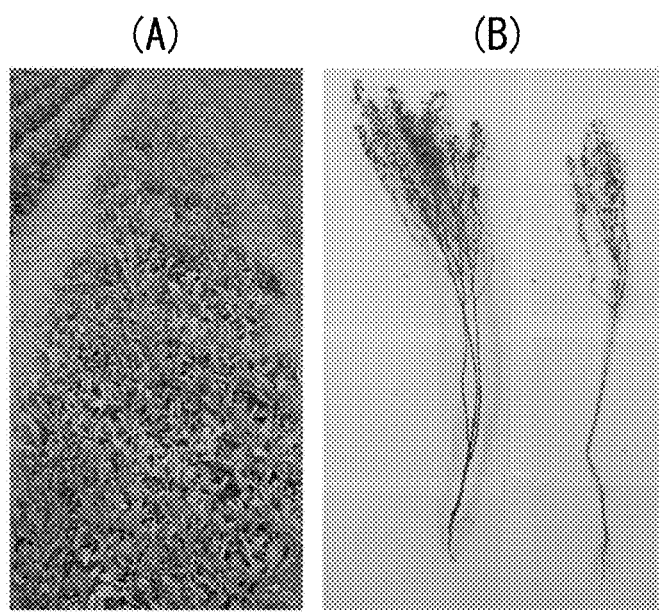
FIG. 1(A) is a photograph of camelina cultivated using compost according to the invention. (B) is a photograph of harvested camelina. The test plot is shown at left, and the control plot is shown at right.

According to one aspect of the invention there is provided a composition for improving soil plant productivity which comprises a bacterium belonging to *Rhizobium* (Rhizobiales).

According to the invention, "improving soil plant productivity" means that growth of plants in the soil is promoted, thereby increasing the plant yield, such as the number of sheaths per plant, the number of seeds per plant and/or the plant body weight.

*Rhizobium* (Rhizobiales) is a major order in the class of alpha proteobacteria, comprising more than 17 families and 130 genera. *Rhizobium* (Rhizobiales) includes a large variety of species. Species that are symbiotic with plants include those that form nodules that are of agricultural importance because they supply nitrogen to plants. Examples of agriculturally important *Rhizobium* species include $N_2$-fixing bacteria *Rhizobium* species that can form nodules on the roots of Leguminosae plants by symbiotic nitrogen fixation and convert atmospheric $N_2$ to ammonia, which can be used as a nitrogen source by plants unlike atmospheric $N_2$.

The concentration of bacteria belonging to *Rhizobium* (Rhizobiales) in the composition of the invention will typically be $10^6$ CFU/g or greater, and is suitably $10^7$ CFU/g or greater and optimally $10^8$ CFU/g or greater.

The composition of the invention may be in either solid or liquid form, and it may include a carrier providing various properties including increased stability, wettability and dispersibility, in addition to the bacterium belonging to *Rhizobium* (Rhizobiales) as the active component. The carrier will typically be an agricultural carrier, and may be soil, a plant growth medium, water, a fertilizer, a plant-based oil or a moistening agent, or a combination thereof.

According to another aspect of the invention there is provided a method for improving soil plant productivity which includes addition of a bacterium belonging to *Rhizobium* (Rhizobiales) to soil.

A bacterium belonging to *Rhizobium* (Rhizobiales) can be added to soil by adding the composition of the invention before planting of the plant, or by mixing with the soil during planting.

The plant with improved productivity achieved by this method is not particularly restricted, but will typically be a crop, such as a plant of Brassicaceae, Poaceae, Leguminosae, Compositae, Solanaceae, Rosaceae, Cucurbitaceae or Convolvulaceae, and preferably a Brassicaceae plant. Brassicaceae plants include camelina and komatsuna. Camelina, in particular, is a crop that has been cultivated since ancient times in Europe for its oil, and in addition to its traditional agricultural advantages including high oil productivity, short-period maturation, low requirement for water and nutrients and resistance to pathogens and pests, in recent years its oil has become a subject of interest as a biofuel material. Numerous test flights of fighter and passenger jets have actually been carried out using biojet fuel produced from camelina oil, and no problems have been reported in terms of performance. Gene recombination testing and cultivation testing for determining optimization of soil components and seeding periods have been conducted in various countries with the goal of increasing camelina yields, and it is thought that camelina oil is an effective candidate as a biofuel starting material.

By improving soil plant productivity it becomes possible to increase the number of sheaths per plant, the number of seeds per plant and/or plant body weight.

According to another aspect of the invention there is provided a compost comprising a bacterium belonging to *Rhizobium* (Rhizobiales), and a bacterium belonging to *Actinomyces* (Actinomycetales), a bacterium belonging to *Bacillus* (Bacillales), a bacterium belonging to Gaiellales, a bacterium belonging to *Myxococcus* (Myxococcales), a bacterium belonging to iii1-15, a bacterium belonging to Solirubrobacterales, a bacterium belonging to *Xanthomonas* (Xanthomonadales), a bacterium belonging to *Burkholderia* (Burkholderiales) and a bacterium belonging to Gemmatales.

Bacteria belonging to *Rhizobium* (Rhizobiales) are typically bacteria belonging to *Rhodoplanes, Bradyrhizobium* or *Pedomicrobium*, such as *Rhodoplanes elegans* or *Methylobacterium adhaesivum*. Bacteria belonging to *Actinomyces* (Actinomycetales) are typically bacteria belonging to *Terracoccus, Mycobacterium* or *Streptomyces*, such as *Actinomadura vinacea, Rathayibacter caricis* or *Actinoallomurus iriomotensis*. Bacteria belonging to *Bacillus* (Bacillales) are typically bacteria belonging to *Bacillus, Rummelii bacillus* or *Planifilum*, such as *Bacillus cereus, Paenibacillus chondroitinus* or *Bacillus clausii*. Bacteria belonging to Gaiellales are typically bacteria belonging to the family Gaiellaceae or AK1AB1 02E. Bacteria belonging to *Myxococcus* (Myxococcales) are typically bacteria belonging to *Sorangium, Plesiocystis* or *Nannocystis*, such as *Sorangium cellulosum*. Bacteria belonging to iii1-15 are typically bacteria belonging to the family RB40 or mb2424. Bacteria belonging to Solirubrobacterales are typically bacteria belonging to the genus *Conexibacter*. Bacteria belonging to *Xanthomonas* (Xanthomonadales) are typically bacteria belonging to *Steroidobacter, Luteimonas* or *Dokdonella*, such as *Stenotrophomonas acidaminiphila* or Pseudoxanthomonas *mexi-* cana. Bacteria belonging to *Burkholderia* (Burkholderiales) are typically bacteria belonging to *Burkholderia*, *Polaromonas* or *Methylibium*. Bacteria belonging to Gemmatales are typically bacteria belonging to the genus *Gemmata*.

The abundance ratio of bacteria in compost is not particularly restricted so long as plant productivity is improved, but preferably the abundance ratio of bacteria belonging to *Rhizobium* (Rhizobiales) is 9% or higher and the abundance ratio of bacteria belonging to iii1-15 is 6% or lower.

Composting may be carried out using a customary method in the field, usually mixing a composting material such as sludge, livestock feces and urine, straw or hay with aerobic microorganisms that decompose them, and fermenting the mixture under aerobic conditions. Factors such as the water content, pH, carbon and nitrogen ratio (C/N ratio), temperature and oxygen all affect the organic decomposition rate in composting, and it is important for such factors to be managed because they can lead to nitrogen starvation of crops.

If the water content of compost is about 60% or greater the tentative density will be high and the adhesion will be increased, making it more difficult to carry out bagging and transport. If the water content is about 30% or lower, on the other hand, more dust will tend to be generated. Since drying of incomplete composting halts decomposition and results in immature compost, drying is preferably carried out after composting has been completed. The water content of the compost will typically by about 30 to 60%, and is preferably about 25 to 55%.

Acidic compost can result in excess mineral concentration, phosphate fixing and absorption problems, and therefore the pH of the compost is preferably about 5.5 to 8.5.

The amount of ions (EC) such as potassium, sodium, chloride and nitrate ions in compost is preferably as low as possible. It is preferably about 3.0 dS/m or lower for bark compost, or about 5.0 dS/m or lower for livestock feces and urine.

Since an excessively high ratio of carbon and nitrogen (C/N ratio) in the compost can potentially cause nitrogen starvation of the soil, it is preferably about 10 to 40. However, since the C/N ratio is determined by simultaneously measuring both easily decomposable organic and poorly decomposable organic carbon and nitrogen, the C/N ratio of sawdust, for example, may be very high at about 340 to 1250, and the C/N ratio of compost mixed with sawdust as a subsidiary material also tends to increase.

Ammonia is generated at the initial stage of composting and can produce bad odor or inhibit crop growth, and therefore a lower ammonia/nitrogen ratio in compost is preferred. A larger value is desirable for nitrate nitrogen, on the other hand, as the proportion of nitrate nitrogen constituting the inorganic nitrogen in compost. Nitrate nitrogen results from nitrification of ammonia, the reaction occurring mainly during secondary fermentation.

It is preferred to have a lower fertilizer component balance in compost (the proportion of potassium, where the total nitrogen amount is 1), with the optimal value being 5 or lower. Heavy metals (especially copper and zinc) are essential for crops in trace amounts but toxic when in excess, and therefore the optimal values for these heavy metal concentrations in compost are 300 ppm or lower for copper and 900 ppm or lower for zinc.

The compost of the invention has very high productivity for the plants mentioned above.

According to another aspect of the invention there is provided a composition for increasing the antioxidant activity of plants, comprising a bacterium belonging to *Bacillus* (Bacillales), *Promicromonospora* or *Olivibacter*.

Plant productivity is significantly reduced depending on abiotic environmental stresses such as strong light, dryness, temperature, salt, heavy metals and ozone. and biological environmental stress such as disease. Such environmental stresses can result in plant withering as it is associated with oxidative stress (injury) due to build-up of reactive oxygen species (ROS). It is known that when a plant suffers oxidative stress, the change in the state of intracellular redox which is dependent on the balance between production and elimination of ROS acts as a signal to initiate the defense system of the environmental stress response, and is associated with programmed cell death or suppressing physiological phenomena such as growth and development, but the present inventors have found, surprisingly, that bacteria belonging to the genera *Bacillus* (Bacillales), *Promicromonospora* and *Olivibacter* increase antioxidant activity in plants.

Bacteria belonging to *Bacillus* (Bacillales) are preferably *Bacillus cereus* bacteria, and most preferably of the bacterial strain deposited at the NITE Patent Microorganisms Depositary as deposit number NITE BP-02974. Bacteria belonging to *Promicromonospora* are preferably *Promicromonospora citrea* bacteria, and most preferably of the bacterial strain deposited at the NITE Patent Microorganisms Depositary as deposit number NITE BP-03025. Bacteria belonging to *Olivibacter* are preferably *Olivibacter* sp. bacteria, and most preferably of the strain deposited at the NITE Patent Microorganisms Depositary as deposit number NITE BP-03026.

Increasing the antioxidant activity of a plant can significantly improve both plant productivity associated with oxidative stress and harvest quality (such as functionality, disease resistance and storage life).

The present invention will now be explained in greater detail by the following examples. It is to be understood, however, that the invention is not restricted in any way to the examples, and various modifications thereof may be implemented.

EXAMPLES

Example 1: Cultivation Test of Camelina 1.1 Cultivation Conditions

Cultivation of camelina (*Camelina sativa*) was in a field in Shibukawa City, Gunma Prefecture (36.53N, 139.01E) from March 25 to Jun. 24, 2018. The camelina variety was Calena. Compost produced by the method described below was spread over the field at 1.5 kg/m$^2$, with no other chemical fertilizer used. The number of sheaths and seed yield were measured during harvesting, and compared with other cultivated harvest yields. Cultivation was with a test plot of 15 m$^2$ and a control plot of 1 m$^2$. The cultivation density in the test plot was 167/m2, and the cultivation density in the control plot was 169/m2

1.2 Production of Compost

The compost used for camelina cultivation was produced in the following manner. Pig feces were used as the starting material for the compost used in the test plot, sawdust was used as the subsidiary material, and original isolated and cultured *Rhizobium* (Rhizobiales) bacteria were used as the added bacteria. The pig feces, bacterial culture solution and sawdust were mixed prior to starting composting. The water content was adjusted to approximately 60% with sawdust and the mixture was constantly stirred and used as compost for a period of three months. The compost used for the control plot was produced by the same method but without addition of bacteria.

1.3 Post-Cultivation Analysis of Soil

The soil components were analyzed by the following methods, with reference to Japan Soil Association (2010). Total nitrogen (N): MacroCorder (JM1000CN), total phosphate (P): nitrate-perchlorate decomposition, ammonium vanadomolybdate method, total potassium (K): nitrate-perchlorate decomposition, atomic absorption spectroscopy, total lime (Ca): nitrate-perchlorate decomposition, atomic absorption spectroscopy, total magnesium (Mg): nitrate-perchlorate decomposition, atomic absorption spectroscopy.

1.4 Cultivated Soil Microflora Analysis by Next-Generation Sequencing

A VD-250R freeze dryer (Taitec) was used for freeze-drying of the cultivated soil sample. A Shake Master Neo (bms) was used for grinding of the freeze-dried sample. An MPure Bacterial DNA Extraction Kit (MP Bio) was used for DNA extraction from the ground sample. Library construction was by 2-step tailed PCR. For primary PCR, the primers 1st_515F_MIX (5'-ACACTCTTTCCCTACACGACGCT-CTTCCGATCT-NNNNN-GTGCCAGCMGCCGCGGT-AA-3': SEQ ID NO: 1) and 1st_806R_MIX (5'-GTGACTG-GAGTTCAGACGTGTGCTCTTCCGATCT-NNNNN-GGACTACHVGGGTWTCTAAT-3': SEQ ID NO: 2) were used, with the 16S rRNA gene variable region V4 (approximately 250 bp) as the target. The primer used during sequence analysis was a mixed primer having random sequences of different lengths of 0 to 5 bases inserted for improved quality. After purification of the primary PCR product, for secondary PCR, the primers 2nd F (5'-AATGA-TACGGCGACCACCGAGATCTACAC-Index2(TATAG-CCT)-ACACTCTTTCCCTACACGACGC-3': SEQ ID NO: 3) and 2nd R (5'-CAAGCAGAAGACGGCATACGAGAT-Index1(GCAGCGTA)-GTGACTGGAGTTCAGACGTG-TG-3': SEQ ID NO: 4) linked to common sequences at both ends of the primary PCR product and having sample-identifying indexes attached were used for amplification of the primary PCR product. Each PCR product was purified with Agencourt AMPure XP (Beckman Coulter). The obtained library was subjected to sequence analysis using MiSeq (Illumina).

The nucleotide sequence data obtained by the sequencing was analyzed in the following manner. Using a Fastx Toolkit, fastq_barcode_splitter, the only sequences extracted were those where the initial reading completely matched the primers. The primer sequences of the extracted sequences were deleted. Sequences with a quality value of <20 were eliminated, and sequences of ≤40 base length and their pair sequences were discarded. Sequences that passed quality filtering were merged using the paired end merge script FLASH. The merging conditions were a merged fragment length of 260 base nucleotides, a lead fragment length of 230 nucleotides and a minimum overlap length of 10 nucleotides. The merged sequences were filtered by fragment length and only those from 246 nucleotides and 260 nucleotides were used for further analysis. All of the filtered sequences were checked by chimeric sequence-checking using the UCHIME algorithm of USEARCH. The database used was 97% OTU of the Greengene accessory of the QIIME pipeline for fungal flora analysis, and all of the sequences judged not to be chimeric were extracted and used for further analysis. OTU creation and line Estimation were carried out using the workflow script of QIIME.

2.1 Cultivation Results

Figure 2:
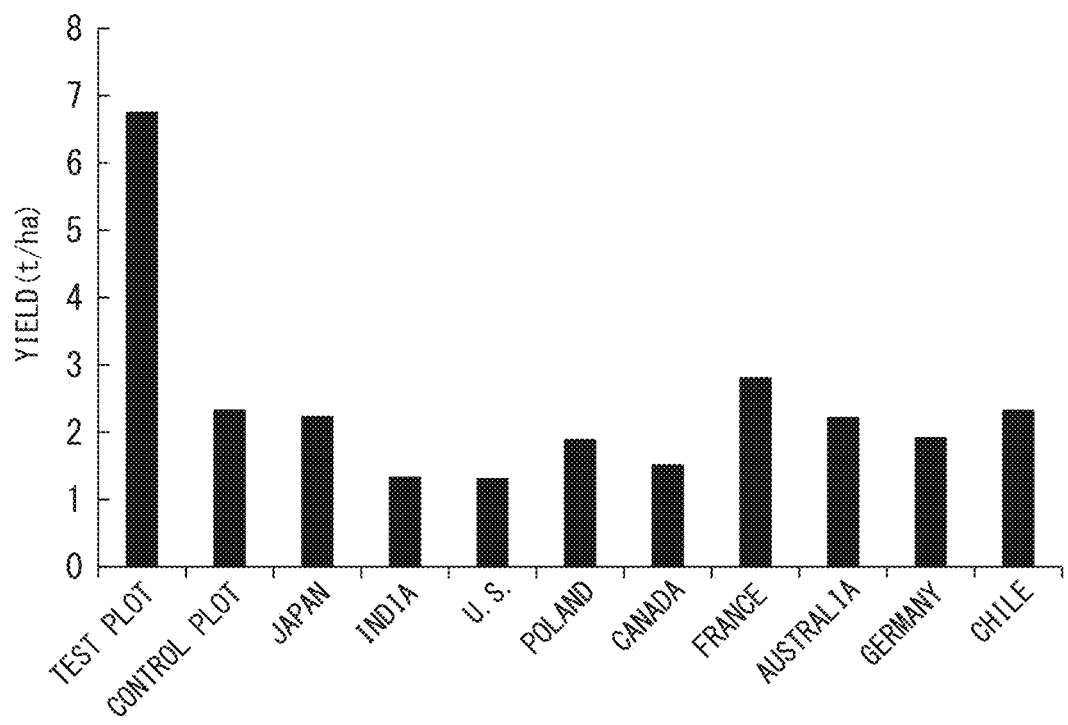
FIG. 2 shows comparison between the test plot and control plot for yields of camelina in (country names): Japan (NPL 2), India (NPL 3), U.S. (NPL 4), Poland (NPL 5), Canada, France, Australia, Germany and Chile (NPL 6).
Figure 3:
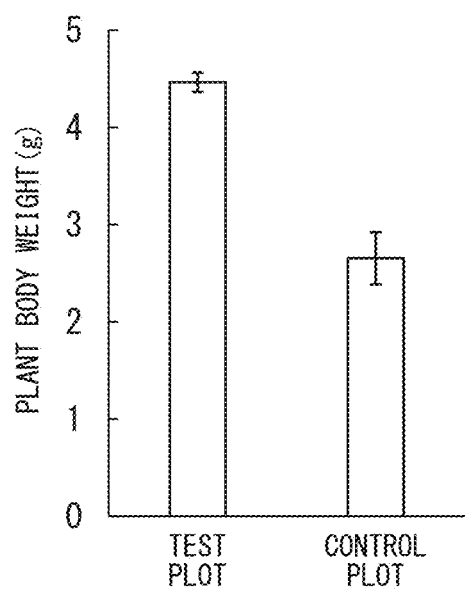
FIG. 3 shows comparison between plant body weights of komatsuna for the test plot and control plot. The error bars represent standard error (n=6). A difference on the level of 1% by Student's t test between the two plots is significant.

Compost with addition of *Rhizobium* (Rhizobiales) as a bacterium correlated with soil productivity was used for cultivation. FIG. 1 shows the state of camelina during cultivation and the strains of the test plot and strains of the control plot after harvesting. FIG. 2 and Table 1 show the results of comparing cultivation yield according to the invention with domestic and international cultivation yields. The results confirm that the number of sheaths per plant were several times greater than the other cultivation products, except for the cultivation example in India. Since the number of seeds per pod according to the invention was moderate, this suggests that the number of seeds per plant increased. No major difference was seen in seed weight compared to the other cultivation results, suggesting that the seed yield per plant had increased. This is clearly seen in the photograph of FIG. 1(B). The cultivation density was also moderate at 6.75 t/ha, indicating that the final yield per area had increased. FIG. 2 shows that the value was greater than any of the domestic or international cultivation examples, being more than 2.4 times compared to the maximum yield of 2.8 t/ha in France.

TABLE 1

Comparison of cultivation results for camelina

| | Test plot | Control plot | Japan (Fujita et al., 2014) | India (Joshi et al., 2017) | India (Kumar et al., 2012) | Poland (Czarnik et al., 2017) |
|---|---|---|---|---|---|---|
| No. sheaths/plant | 489 | 158 | 183 | 143 | 734 | 65.1 |
| No. seeds/sheath | 9.32 | 9.47 | 8.8 | 12.9 | 19.2 | 9 |
| No. seeds/plant | 4513 | 1496 | 1610 | 1844 | 14089 | 585 |
| Weight/100 seeds (g) | 0.898 | 0.917 | 0.906 | — | 0.94 | 0.93 |
| Seed yield (g/plant) | 4.04 | 1.37 | 1.6 | — | 7.44 | 0.545 |
| Cultivation density (plants/m$^2$) | 167 | 169 | 139 | — | 17.6 | 354 |
| Seed yield (t/ha) | 6.75 | 2.31 | 2.22 | 0.722 | 1.31 | 1.87 |

2.2 Soil Microflora Analysis

DNA extracted from soil was supplied to next-generation sequencing for analysis of the microflora in the soil. In the test plot, the added bacterium *Rhizobium* (Rhizobiales) was detected in the greatest amount, at 9.42% of the total. The highly detected bacteria other than *Rhizobium* (Rhizobiales) were *Actinomyces* (Actinomycetales) (7.61%), *Bacillus* (Bacillales) (7.02%), Gaiellales (6.58%), *Myxococcus* (Myxococcales) (4.89%), iii1-15 (3.32%), Solirubrobacterales (3.09%), *Xanthomonas* (Xanthomonadales) (2.40%), *Burkholderia* (Burkholderiales) (2.33%) and Gemmatales (2.30%).

The *Rhizobium* (Rhizobiales) detected in the control plot was 5.75% of the total, which was lower than in the test plot. The other highly detected bacteria other were *Actinomyces* (Actinomycetales) (7.52%), Gaiellales (7.21%), *Bacillus* (Bacillales) (6.01%), *Myxococcus* (Myxococcales) (5.11%), iii1-15 (3.26%), Solirubrobacterales (3.25%), *Burkholderia* (Burkholderiales) (2.53%), Gemmatales (2.45%) and *Nitrososphaera* (Nitrososphaerales) (2.42%).

With camelina cultivation, it has been shown that the number of sheaths per plant and the seed weight tend to increase with increasing cultivation density (NPL 5). The yield per strain was a very high value in the cultivation example in India, but this was the result of exceedingly low density (17.6 plants/m2), and the yield per unit area was lower at 1.31 t/ha. In this experiment, the cultivation density was at moderate density but the number of sheaths per plant was high. As a result, the yield per unit area was very high at 6.75 t/ha. The yield per unit area in the control plot, on the other hand, was not much different from existing cultivation examples.

Based on the results of soil microflora analysis with compost spreading, *Rhizobium* (Rhizobiales) was detected in the highest concentration at 9.42% of the total, which was also increased compared to the control plot. The results shown here suggest bacterial addition to compost increased *Rhizobium* (Rhizobiales) in the soil and contributed to improved soil productivity.

Focusing on the 4 bacteria types *Rhizobium* (Rhizobiales) and iii1-15, which exhibit a positive correlation with soil productivity, and *Acidobacterium* (Acidobacteriales) and *Solibacterium* (Solibacterales) which exhibit a negative correlation, the bacterial concentrations were compared between the test plot and control plot, as well as in the 12 locations reported in NPL 1. The results are shown in Table 2. Table 3 is a correspondence table of latitude and longitude with the codes representing the soils and collection locations of NPL 1.

TABLE 2

Correlation wherein bacterial abundance ratio and soil productivity

| | Abundance ratio of bacteria with positive correlation (%) | | Abundance ratio of bacteria with negative correlation (%) | |
|---|---|---|---|---|
| | Rhizobiales | iiiI-15 | Acidobacteriales | Solibacterales |
| Test plot | 9.42 | 3.32 | 0.82 | 1.02 |
| Control plot | 5.75 | 3.26 | 1.10 | 1.26 |
| OR | 5.70 | 2.60 | 6.39 | 6.51 |
| ST | 6.21 | 4.02 | 4.19 | 3.81 |
| M4 | 5.58 | 2.81 | 4.40 | 3.64 |
| M9 | 8.71 | 3.99 | 3.02 | 2.86 |
| H | 5.44 | 1.29 | 9.31 | 4.63 |
| N | 5.39 | 4.35 | 2.42 | 2.63 |
| IZ | 8.22 | 4.45 | 1.87 | 2.16 |
| SE | 3.74 | 1.54 | 3.23 | 3.99 |
| SI | 3.69 | 4.35 | 0.65 | 2.36 |
| OG | 7.00 | 5.67 | 1.58 | 1.71 |
| Y | 5.76 | 2.74 | 6.07 | 2.72 |
| IM | 10.80 | 6.19 | 0.11 | 0.84 |

TABLE 3

Soil collection location

| | Latitude | Longitude |
|---|---|---|
| OR | 43.16 | 140.78 |
| ST | 42.87 | 143.36 |
| M4 | 42.62 | 140.79 |
| M9 | 42.62 | 140.79 |
| H | 40.85 | 140.67 |
| N | 40.55 | 140.55 |
| IZ | 39.32 | 141.45 |
| SE | 35.84 | 139.54 |
| SI | 35.85 | 139.56 |
| OG | 35.9 | 138.53 |
| Y | 35.86 | 138.39 |
| IM | 34.8 | 137.01 |

The abundance ratios of the 4 bacterial types in soil were compared between the 12 locations and the test plot and control plot. In the soil of the test plot in the 14 soils, *Rhizobium* (Rhizobiales) was high in the 2nd (9.42%) and iii1-15 was high in the 8th (3.32%). *Acidobacterium* (Acidobacteriales) was low in the 3rd (0.82%) and *Solibacterium* (Solibacterales) was low in the 2nd (1.02%). In the soil of the control plot, among the 14 soils, *Rhizobium* (Rhizobiales) was high in the 8th (5.75%), which was still lower than the test plot. As regards the abundance ratio of bacteria other than *Rhizobium* (Rhizobiales), iii1-15 was high in the position 9th (3.26%), *Acidobacterium* (Acidobacteriales) was low in the 4th (1.10%) and *Solibacterium* (Solibacterales) was low in the 3rd (1.26%). Overall, the soils of the test plot had very high productivity for the bacterial compositions.

When compost with added bacteria was used for cultivation of camelina in the same test and compared to existing domestic and international reports, it was confirmed that yields of at least 2.4-fold per unit area were obtained. When the bacteria in the soil were analyzed, the added bacteria were observed to be highly abundant. A method was thus discovered that offers the potential for manipulating soil microflora for cultivation by addition of specific bacteria during compost production to increase product yields.

Example 2. Komatsuna Cultivation Test

The compost used for komatsuna cultivation was produced in the following manner. Pig feces, sawdust and original isolated and cultured *Rhizobium* (Rhizobiales) bacterial culture solutions were used as materials for the compost used in the test plot. The pig feces, bacterial culture solution and sawdust were mixed prior to starting composting. The water content was adjusted to 60% with sawdust and the mixture was constantly stirred and used as compost for a period of three months. The compost used for the control plot was produced by the same method but without addition of bacteria.

The produced compost was provided for a cultivation test of komatsuna (*Brassica rapa* var. *perviridis*). For the komatsuna pot cultivation test, the produced compost was mixed with akadama soil at 3:7. A chemical fertilizer containing 8% each of ammonia nitrogen, soluble phosphates and water-soluble potassium was used at 0.84 g per 1 L of soil. The cultivation was carried out from seeds at room temperature with fluorescent lamp lighting, and the growth was periodically observed.

For this test, compost was produced using *Rhizobium* (Rhizobiales), and the Brassicaceae komatsuna cultivation test was carried out in the same manner as for camelina. Cultivation of komatsuna using the bacteria-added compost resulted in an increase in plant body weight of about 1.7-fold.

Example 3. Evaluation of Komatsuna Antioxidant Power 3.1 *Bacillus Cereus*

The bacterial strain 2764-01-S16 of *Bacillus cereus* isolated by the applicant (deposit number: NITE BP-02974) was inoculated for the cultivation test of komatsuna. Specifically, the bacterial inoculation was carried out by immersing the 10th-day vermiculite-cultivated komatsuna seedling roots in bacterial suspension for about 30 seconds. Sterilized water was used for the control plot. The cultivation was carried out using steam-sterilized field soil and vermiculite mixed at 1:1, and with liquid fertilizer applied about once per week. Cultivation was carried out in a vinyl plastic-covered greenhouse.

The edible part of the cultivated komatsuna was used as the analysis sample and cut to 1 cm-square, and then mixed with a 4-fold weight of water, broken up with a juicer and heated at 80° C. for 30 minutes, after which it was cooled and filtered to prepare a sample solution. After mixing 25 μL of sample solution, 50 μL of 44.4 mM 2,2,6,6-tetramethyl-4-piperidone (TMPD), 100 μL of 2.5 mM dimethyl sulfoxide (DMSO) and 50 μL of 55.5 mM riboflavin, the liquid mixture was irradiated with ultraviolet rays for 20 seconds, and the singlet oxygen scavenging activity of the sample solution was measured by the electron spin resonance (ESR) method with the measuring conditions set to Field=336.4±5 mT (magnetic field range), Power=3 mW, Modulation Width=0.1 mT, Sweep Time=1 min, Time Constant=0.1 sec, Amplify=250, to evaluate the antioxidant power of the komatsuna.

The strength of radicals captured by the scavenger TMPD can be measured based on the obtained signal. The actual amount of substance can be estimated based on the strength, from a calibration curve previously prepared using histidine as the standard substance for determining singlet oxygen scavenging activity (antioxidant power). High antioxidant power of a sample results in more elimination of radicals so that they are not scavenged by the scavenger, producing a lower signal.

When the weight and antioxidant power were compared with a komatsuna strain without bacterial inoculation, the weight of the non-inoculated komatsuna strain was 3.15 g and the antioxidant power was 1560 μmol histidine/g, while the weight of the inoculated komatsuna strain was 4.07 g and the antioxidant power was 1890 μmol histidine/g, indicating significant improvement in weight and antioxidant power in the inoculated komatsuna strain.

3.2 *Promicromonospora citrea*

The bacterial strain 27624-02-C06 of *Promicromonospora citrea* (deposit number: NITE BP-03025) isolated by the applicant was inoculated into komatsuna and a cultivation test of the komatsuna was conducted. Specifically, the bacterial inoculation was carried out by immersing the 10th-day vermiculite-cultivated komatsuna seedling roots in bacterial suspension for about 30 seconds. Sterilized water was used for the control plot. The cultivation was carried out using steam-sterilized field soil and vermiculite mixed at 1:1, and with liquid fertilizer applied about once per week. Cultivation was carried out in a vinyl plastic-covered greenhouse.

The edible part of the cultivated komatsuna was used as the analysis sample and cut to 1 cm-square, and then mixed with a 4-fold weight of water, broken up with a juicer and heated at 80° C. for 30 minutes, after which it was cooled and filtered to prepare a sample solution. After mixing 50 μL of sample solution, 20 μL of 5.7 M 5,5-dimethyl-1-pyrroline N-oxide (DMPO) and 90 μL of 2.5 mM hydrogen peroxide, the liquid mixture was irradiated with ultraviolet rays for 30 seconds, and the hydroxy radical scavenging activity of the sample solution was measured by ESR with the measuring conditions set to Field=335±5 mT, Power=3 mW, Modulation Width=0.1 mT, Sweep Time=1 min, Time Constant=0.1 sec, Amplify=50, to evaluate the antioxidant power of the komatsuna.

The strength of radicals captured by the scavenger DMPO can be measured based on the obtained signal. The actual amount of substance can be estimated based on the strength, from a calibration curve previously prepared using DMSO as the standard substance for determining hydroxy radical scavenging activity (antioxidant power). High antioxidant power of a sample results in more elimination of radicals so that they are not scavenged by the scavenger, producing a lower signal.

When the weight and antioxidant power were compared with a komatsuna strain without bacterial inoculation, the weight of the non-inoculated komatsuna strain was 3.51 g and the antioxidant power was 1670 μmol DMSO/g, while the weight of the inoculated komatsuna strain was 4.29 g and the antioxidant power was 2350 μmol DMSO/g, indicating significant improvement in weight and antioxidant power in the inoculated komatsuna strain.

3.3 *Olivibacter* sp.

The bacterial strain 27624-02-C07 of *Olivibacter* sp. isolated by the applicant (deposit number: NITE BP-03026) was inoculated for the cultivation test of komatsuna. Specifically, the bacterial inoculation was carried out by immersing the 10th-day vermiculite-cultivated komatsuna seedling roots in bacterial suspension for about 30 seconds. Sterilized water was used for the control plot. The cultivation was carried out using steam-sterilized field soil and vermiculite mixed at 1:1, and with liquid fertilizer applied about once per week. Cultivation was carried out in a vinyl plastic-covered greenhouse.

The edible part of the cultivated komatsuna was used as the analysis sample and cut to 1 cm-square, and then mixed with a 4-fold weight of water, broken up with a juicer and heated at 80° C. for 30 minutes, after which it was cooled and filtered to prepare a sample solution. After mixing 50 μL of sample solution, 30 μL of 8.55 M 5,5-dimethyl-1-pyrroline N-oxide (DMPO), 50 μL of 1.25 mM hypoxanthine, 20 μL of 4.37 mM dimethyl sulfoxide (DMSO) and 50 μL of 0.1 U/ml xanthine oxidase, the liquid mixture was stirred for 60 seconds for reaction, and the superoxide radical scavenging activity of the sample solution was measured by ESR with the measuring conditions set to Field=335±5 mT, Power=3 mW, Modulation Width=0.079 mT, Sweep Time=1 min, Time Constant=0.1 sec, Amplify=250, to evaluate the antioxidant power of the komatsuna.

The strength of radicals captured by the scavenger DMPO can be measured based on the obtained signal. The actual amount of substance can be estimated based on the strength, from a calibration curve previously prepared using the superoxide dismutase as the standard substance for determining superoxide radical scavenging activity (antioxidant power). High antioxidant power of a sample results in more elimination of radicals so that they are not scavenged by the scavenger, producing a lower signal.

When the weight and antioxidant power were compared with a komatsuna strain without bacterial inoculation, the weight of the non-inoculated komatsuna strain was 3.51 g and the antioxidant power was 122 units SOD/g, while the weight of the inoculated komatsuna strain was 4.47 g and the antioxidant power was 190 units SOD/g, indicating significant improvement in weight and antioxidant power in the inoculated komatsuna strain.

Strain 2764-01-S16 has been deposited at the independent administrative institution: National Institute of Technology and Evaluation, NITE Patent Microorganisms Depositary (Address: Room No. 122, 2-5-8 Kazusa Kamatari, Kisarazu City, Chiba Prefecture, 292-0818 Japan), as deposit number NITE BP-02974 (Original deposit date: Jun. 20, 2019). Strain 27624-02-C06 has been deposited as deposit number NITE BP-03025 (original deposit date: Sep. 20, 2019), and strain 27624-02-C07 has been deposited as deposit number NITE BP-03026 (original deposit date: Sep. 20, 2019).

[Deposit Numbers]

NITE BP-02974

NITE BP-03025

NITE BP-03026

[Sequence Listing]

The invention claimed is:

1. A plant inoculated with an isolated bacterial strain of *Promicromonospora citrea*, wherein the bacterial strain is deposited at the NITE Patent Microorganisms Depositary as deposit number NITE BP-03025, and wherein the inoculated plant has greater antioxidant activity than the plant prior to inoculation.

* * * * *

```
                              SEQUENCE LISTING

<160> NUMBER OF SEQ ID NOS: 4

<210> SEQ ID NO 1
<211> LENGTH: 57
<212> TYPE: DNA
<213> ORGANISM: Artificial Sequence
<220> FEATURE:
<223> OTHER INFORMATION: 1st_515F_MIX_primer
<220> FEATURE:
<221> NAME/KEY: misc_feature
<222> LOCATION: (34)..(38)
<223> OTHER INFORMATION: n is a, c, g, or t

<400> SEQUENCE: 1
acactctttc cctacacgac gctcttccga tctnnnnngt gccagcmgcc gcggtaa          57

<210> SEQ ID NO 2
<211> LENGTH: 59
<212> TYPE: DNA
<213> ORGANISM: Artificial Sequence
<220> FEATURE:
<223> OTHER INFORMATION: 1st_806R_MIX_primer
<220> FEATURE:
<221> NAME/KEY: misc_feature
<222> LOCATION: (35)..(39)
<223> OTHER INFORMATION: n is a, c, g, or t

<400> SEQUENCE: 2
gtgactggag ttcagacgtg tgctcttccg atctnnnnng gactachvgg gtwtctaat        59

<210> SEQ ID NO 3
<211> LENGTH: 59
<212> TYPE: DNA
<213> ORGANISM: Artificial Sequence
<220> FEATURE:
<223> OTHER INFORMATION: 2nd F_primer

<400> SEQUENCE: 3
aatgatacgg cgaccaccga gatctacact atagcctaca ctctttccct acacgacgc        59

<210> SEQ ID NO 4
<211> LENGTH: 54
<212> TYPE: DNA
<213> ORGANISM: Artificial Sequence
<220> FEATURE:
<223> OTHER INFORMATION: 2nd R_primer

<400> SEQUENCE: 4
caagcagaag acggcatacg agatgcagcg tagtgactgg agttcagacg tgtg             54
```